United States Patent
King (10) Patent No.: US 8,165,681 B2
(45) Date of Patent: Apr. 24, 2012

(54) METHOD FOR BLOCKING ACTIVATION OF TISSUE OR CONDUCTION OF ACTION POTENTIALS WHILE OTHER TISSUE IS BEING THERAPEUTICALLY ACTIVATED

(75) Inventor: Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 1207 days.

(21) Appl. No.: 11/930,725

(22) Filed: Oct. 31, 2007

(65) Prior Publication Data

US 2008/0058888 A1     Mar. 6, 2008

Related U.S. Application Data

(63) Continuation of application No. 11/054,836, filed on Feb. 10, 2005, now Pat. No. 7,433,734, which is a continuation of application No. 09/859,280, filed on May 17, 2001, now Pat. No. 6,928,320.

(51) Int. Cl.
*A61N 1/36* (2006.01)

(52) U.S. Cl. .............................. 607/40; 607/41; 607/71
(58) Field of Classification Search .................. None
See application file for complete search history.

(56) References Cited

U.S. PATENT DOCUMENTS

| | | | | |
|---|---|---|---|---|
| 4,622,973 A | * | 11/1986 | Agarwala | 607/48 |
| 5,562,717 A | * | 10/1996 | Tippey et al. | 607/41 |
| 2002/0055779 A1 | * | 5/2002 | Andrews | 623/11.11 |

* cited by examiner

Primary Examiner — Kennedy Schaetzle (57) ABSTRACT

A desired effect is produced by therapeutically activating tissue at a first site within a patient's body and a corresponding undesired side effect is reduced by blocking activation of tissue or conduction of action potentials at a second site within the patient's body by applying high frequency stimulation and/or direct current pulses at or near the second site. Time-varying DC pulses may be used before or after a high frequency blocking signal. The high frequency stimulation may begin before and continue during the therapeutic activation. The high frequency stimulation may begin with a relatively low amplitude, and the amplitude may be gradually increased. The desired effect may be promotion of micturition or defecation and the undesired side effect may be sphincter contraction.

9 Claims, 7 Drawing Sheets

METHOD FOR BLOCKING ACTIVATION OF TISSUE OR CONDUCTION OF ACTION POTENTIALS WHILE OTHER TISSUE IS BEING THERAPEUTICALLY ACTIVATED

RELATED APPLICATIONS

This application is a continuation of U.S. patent application Ser. No. 11/054,836, filed Feb. 10, 2005, now U.S. Pat. No. 7,433,734, issued Oct. 7, 2008, which is a continuation of U.S. patent application Ser. No. 09/859,280, filed May 17, 2001, now U.S. Pat. No. 6,928,320. The entire disclosures of the foregoing applications are incorporated herein by reference.

FIELD OF THE INVENTION

This invention relates to techniques for blocking activation of electrically excitable tissue within a patient's body, and more particularly relates to techniques for producing a desired effect by therapeutically activating tissue at a first predetermined site within a patients body and for reducing a corresponding undesired side effect by blocking activation of tissue at a second predetermined site within the patient's body.

DESCRIPTION OF RELATED ART

It is often desirable to therapeutically activate excitable tissue, such as nerve, muscle, or glandular cells of a patient by electrical stimulation or via medications. An undesirable side effect of such therapeutic activation of excitable tissue is that other tissue, either nearby or distant, may be undesirably activated, either directly by the same mode of activation, or indirectly by sensory feedback or other reflexes.

Generally, undesired action potentials in sensory nerves or dorsal roots may either be disagreeable to the patient or cause contrary effects. When stimulating to assist peristalsis in the esophagus, ureter, stomach, or intestine, co-contraction of sphincters or disagreeable sensations or reverse peristalsis might be undesirable. For instance, if a patient is unable to control urination or defecation, stimulation of peripheral nerves or ventral roots to contract a patient's bladder for micturition or to move bowel contents may be desirable. Such activation, or even lower amplitude stimulation, however, will typically create action potentials in sphincters, such as those in the external urethra or anus. Such action potentials will tend to cause the sphincters to contract, which may result in an inability to pass urine or fecal matter beyond the sphincters. In addition, increased pressure in the bladder caused by simultaneous compression of the patient's bladder and contraction of the patient's external urethral sphincter may lead to injury to the patient, including increased pressure and damage to either or both the bladder and the kidneys. A conventional approach that has been proposed for patients that are substantially paralyzed is to cut the patient's nerves that lead back into the spinal cord (dorsal roots) so that the stimulation of the bladder does not cause a lot of neural activity in the spinal cord. If a patient's bladder is significantly overfilled, autonomic dysreflexia may occur causing a very large and dangerous increase in the patient's blood pressure, which may cause a stroke.

When stimulating to defibrillate a patient's heart, extremely intense pain is typically inflicted upon the patient due to simultaneous activation of many afferent fibers, some of which may even be the axons of nociceptors.

When stimulating certain motorneurons, activations directly or by spinal reflex of antagonistic motorneurons and muscles may interfere with the desired motion, necessitating an increase in the strength of stimulation, which causes increased rigidity of a patient's joints.

Electrical excitation of tissue at low frequencies (e.g., less than 100 Hertz) has been known to cause action potentials in nerve and muscle. In addition, some techniques have been described to block action potentials in certain nerve fibers, with the best observations done in animal experiments.

Tanner (Nature, vol. 195, 1962: 712-713) and Woo & Campbell (Bull. L. A. Neurol. Soc., vol. 29, 1964:87-94) showed that 20,000 Hz stimulation of a nerve is able to block passing action potentials, with larger voltages (amplitudes) needed to progressively block smaller fibers. Recently, from therapeutic stimulation of the brain in patients with tremor and other symptoms of Parkinson's disease, evidence has mounted that high frequency stimulation (100-185 Hertz) keeps neurons depolarized, and hence incapable of producing action potentials (Benabid et al., Lancet, vol. 337, 1991: 403-406; Benazzouz et al., Neurosci. Lett., vol. 189, 1995: 77-80). High frequency stimulation of the spinal cord or nerves (250 Hertz and more) has been anecdotally reported to relieve chronic pain, but whether this works by blocking of action potentials is unknown (Picaza et al., Surg. Neurol., vol. 4, 1975: 105-114 and 115-126; Sheldon et al., Surg. Neurol., vol. 4, 1975: 127-132; Bennett et al., Neuromodulation, vol. 2, 1999: 202-210).

Mendel & Wall (J. Physiol., vol. 172, 1964: 274-294) and Campbell & Woo (Bull. Los Angeles Neurol. Soc., vol. 31, 1966: 63-71) demonstrated a similar amplitude-dependent blocking of action potentials in progressively smaller axons using direct current (D.C.) signals. Recently, evidence has developed that repetitive stimulation in rats of the brain area called the amygdala, which can cause seizures due to kindling, can have its kindling effects quenched by use of 5 to 15 microampere D.C. currents applied once a day for 15 minutes (Weiss et al., Exper. Neurol., vol. 154, 1998: 185-192).

The disadvantage of direct current pulses is that they can lead to tissue or electrode damage (Pudenz, et al, Surg. Neurol., vol. 4, 1975:265-270) or to asynchronous repetitive action potential discharges (Manfredi, Arch. Ital. Biol., vol 108, 1970: 52-71; Sassen & Zimmerman, Pflugers Arch. Gesamte Physiol. Menschen Tiere, vol. 341, 1973: 179-195).

Van den Honert & Mortimer (IEEE trans. BME., vol. 28, 1981: 373-378 and 379-382) developed a technique to create action potentials that propagate in only one direction along axons using a tripolar cuff with three electrodes and two regulated current stimulators. This method was used by Brindley & Craggs (J. Neurol. Neurosurg. Psychiat., vol. 43, 1980: 1083-1090) to excite only the smaller (parasympathetic) fibers in spinal nerve roots and peripheral nerves for bladder emptying. Ungar, Mortimer & Sweeney (Ann. Biomed. Engng, vol. 14, 1986: 437-450) were also able to generate unidirectionally propagating action potentials in nerves using an asymmetric monopolar electrode cuff. However, both of these partial-blocking techniques require complete encirclement of the axons of interest with non-conducting materials, something which the high frequency and D.C. techniques do not require.

In order to minimize undesirable side effects associated with therapeutic activation of tissue, including, but not limited to, the side effects mentioned above, it may be desirable to deactivate or inhibit certain excitable tissue during the time that the desired effect is being produced in the therapeutically activated tissue.

It would, therefore, be desirable to block action potentials in tissue that are deliberately generated from low frequency stimulation. The block may not be complete, and there may be asynchronous, even repetitive generation of some action potentials in the process, but under certain circumstances, it may be possible to prevent most of the action potentials in certain nerves that otherwise may be caused by other electrodes in nearby tissue that use deliberate low frequency pulses to cause action potentials. The volume of tissue recruited near the deliberate "activation" electrodes and the volume of tissue inhibited near the "blocking" electrodes would both depend upon the parameters of stimulation, especially the amplitude and pulse width.

SUMMARY OF THE INVENTION

In accordance with certain inventive principles, a desired effect is produced by therapeutically activating tissue at a first site within a patient's body and a corresponding undesired side effect is reduced by blocking activation of tissue at a second site within the patient's body by applying high frequency stimulation and/or one or more direct current pulses at or near the second site.

In accordance with various inventive principles, the desired effect may be promotion of micturition; the undesired side effect may be sphincter contraction; the first site may be the patient's bladder dome, sacral roots, or pelvic plexus; and the second site may be the patient's: sacral dorsal roots, spinal dorsal columns, conus medullaris, pudendal nerve, hypogastric plexi, or perineal nerve.

The desired effect may be promotion of defecation; the undesired side effect may be sphincter contraction, elevated pelvic floor, or sharp ano-rectal angle; the first site may be the patient's: hypogastric plexus, pelvic plexus, nerves to rectum, sacral roots, pelvic plexus, or rectal muscle; and the second site may be the patient's: sacral dorsal roots, spinal dorsal columns, conus medullaris, pudendal nerve, or nerves to the patient's pelvic floor muscles.

The desired effect may be peristalsis of the patient's esophagus; the undesired side effect may be contraction at the patient's gastroesophageal sphincter; the first site may be the patient's: esophagus, nerves to the patient's esophagus, pharynx, or nerves to the patient's pharynx; and the second site may be the patient's: hiatal esophagus area near the patient's diaphragm, or nerves to the patient's esophagus.

The desired effect may be peristalsis of the patient's ureter; the undesired side effect may be closure of the patient's anti-reflux valves near the patient's bladder trigone; the first site may be the patient's: renal pelvis or a portion of the patient's ureter; and the second site may be the patient's: base of the bladder near an entrance of a ureter, hypogastric plexus, or pelvic plexus.

The desired effect may be peristalsis of the patient's stomach; the undesired effect may be closure of the patient's pyloric sphincter; the first site may be the patient's: stomach wall muscles or the nerves leading to the patient's stomach wall muscles; and the second site may be the patient's: muscle fibers of the pyloric sphincter or nerves to the pyloric sphincter.

The desired effect may be peristalsis of the patient's intestine; the undesired effect may be closure of the patient's ileocecal valve to the patient's colon; the first site may be the patient's: intestinal wall smooth muscle, hypogastric plexus, or nerves to the patient's hypogastric plexus; and the second site may be the patient's: ileocecal valve, mesenteric ganglia, dorsal root, spinal dorsal columns, or splanchnic nerves.

The desired effect may be selected from the group consisting of: defibrillation of the patient's atria or defibrillation of the patient's ventricles; the undesired side effect may be pain; the first site may be near a heart pacing/defibrillation lead: inside the patient's heart chambers or outside the patient's heart chambers; the second site may be the patient's: vagus nerve, branches of the patient's vagus nerve from the patient's heart, thoracic sympathetic nerves, ansa subclavia, sympathetic trunk ganglia (T1-T4), stellate ganglia, cervical ganglia (C1-C8), celiac plexus, brachial plexi, dorsal roots (C1-T4), spinal dorsal columns, or dorsal roots.

The desired effect may be extension of the patient's leg; the undesired side effect may be co-contraction of the antagonist muscles; the first site may be the patient's femoral nerve to the patient's quadriceps femoris; and the second site may be the patient's tibial nerve to the patient's gastrocnemius muscle.

The desired effect may be movement of one of the patient's joints in a predetermined direction; the undesired side effect may be co-contraction of antagonist muscles; the first site may be the patient's peripheral nerve; and the second site may be the patient's nerve branch to an antagonist muscle.

The high frequency blocking stimulation may begin before and continue during the therapeutic activation. The high frequency blocking stimulation may begin with a relatively low amplitude, and the amplitude may be gradually increased. The high frequency blocking stimulation may be terminated by gradually reducing the amplitude of the high frequency stimulation.

A sensor may be included for sensing a state of the tissue at the second site or at a more remote site. Means, responsive to the sensor, for adjusting the pulse amplitude, pulse width, pulse frequency, pulse duty cycle, pulse polarity, or pulse waveform of the high frequency blocking stimulation at the second site may also be included.

Direct current pulses may be used to block activation of the tissue at the second site. If ramped up or down gradually, this may allow neuronal accommodation and prevent action potentials. Direct current pulses may also be used before or after a series of high frequency blocking signals, so that much of the stimulation for blocking has charge balance to protect the electrodes or tissue.

DETAILED DESCRIPTION OF THE INVENTION

Evidence, from stimulation of the brain for tremor and other symptoms of Parkinson's disease, indicates that high frequency stimulation keeps neurons depolarized, and hence incapable of causing an action potential. See A. L. Benabid et al., Long-Term Suppression of Tremor by Chronic Stimulation of the Ventral Intermediate Thalamic Nucleus, the Lancet, vol. 337, 1991, pp. 403-406. Accordingly, the therapies of deep brain stimulation to block tremor and to block neuronal pathways that prevent desired volitional movements (freezing, akinesia, bradykinesia) often use high frequency stimulation. For instance, commonly assigned U.S. Pat. Nos. 5,716,377 and 5,833,709 disclose such systems and methods and are incorporated herein by reference. As used herein, the phrase "high frequency stimulation" refers to electrical stimulation of at least approximately 100-120 Hz, while "low frequency stimulation" refers to electrical stimulation of less than approximately 100 Hz.

Figure 1:
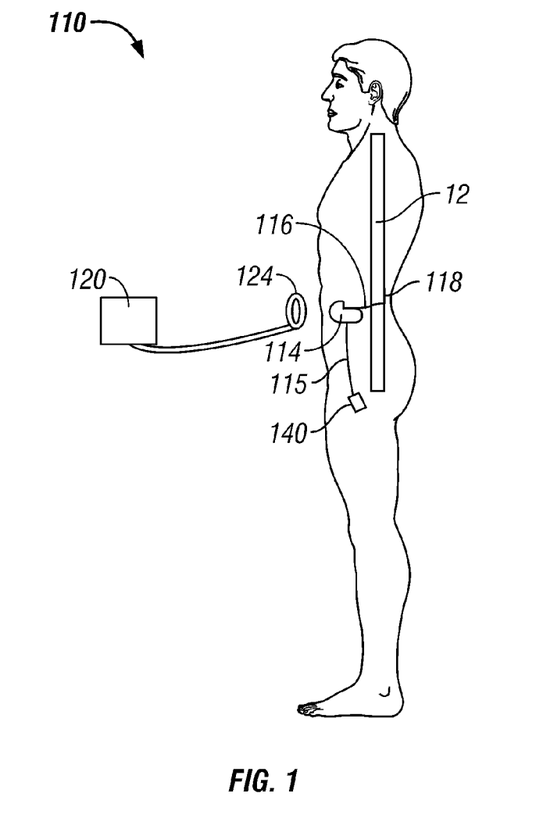
FIG. 1 is a diagrammatic illustration of a system for blocking activation of tissue within a patient according to various inventive principles.

FIG. 1 is a schematic view of a patient 110 having an implant of a neurological stimulation system employing a preferred form of the present invention. A system in accordance with the principles of the invention may employ an implantable pulse generator 114 to produce stimulation pulses to various predetermined sites within a patient's body. For instance, as depicted in FIG. 1, the concept of applying high frequency blocking stimulation with electrode 140 is depicted schematically. High frequency stimulation is applied in order to prevent an undesirable side effect of spinal cord stimulation applied via electrode 118. In accordance with the principles of this invention, the site at which an undesirable side effect is blocked using high frequency stimulation will often be located in close proximity to the location within the patient's body at which low frequency intended effect stimulation is applied. Nevertheless, the two types of stimulation may be applied in areas of a patient's body that are relatively far apart, as shown, for instance, in FIG. 1. Another example is applying high frequency blocking stimulation to block pain perceived by a patient while administering a defibrillation pulse to the patient's heart, the blocking stimulation may be applied in locations away from the heart, as described in more detail below.

In a preferred embodiment, implantable signal generator 114 may be a modified signal generator, such as Model 7424 manufactured by Medtronic, Inc. under the trademark Itrel7, or pulse generator 114 might not have a battery and might instead get programming signals and energy from a modified exterior transmitter 120 and antenna 124 like a radio frequency system manufactured by Medtronic, Inc. known as X-trel7 or Mattrix7. Signal generator 114 could simultaneously produce both high and low frequency stimulation, for instance, at frequencies above and below 100 Hz, respectively. Alternatively, signal generator 114 could output either high or low frequency stimulation and a second signal generator, not shown, could be used to output the other type of stimulation.

For spinal cord stimulation (SCS), signal generator 114 is commonly implanted subcutaneously in a human body in the abdomen or back. In accordance with the principles of this invention, one or more signal generators may be placed near a location that will be therapeutically activated or near an area in which activation will blocked or near both such types of areas. Electrodes 140 and 118 may be operatively coupled to signal generator 114 by leads 115 and 116, respectively. Alternatively, Electrodes 140 and 118 may be operatively coupled to signal generator 114 by a single lead.

Figure 2:
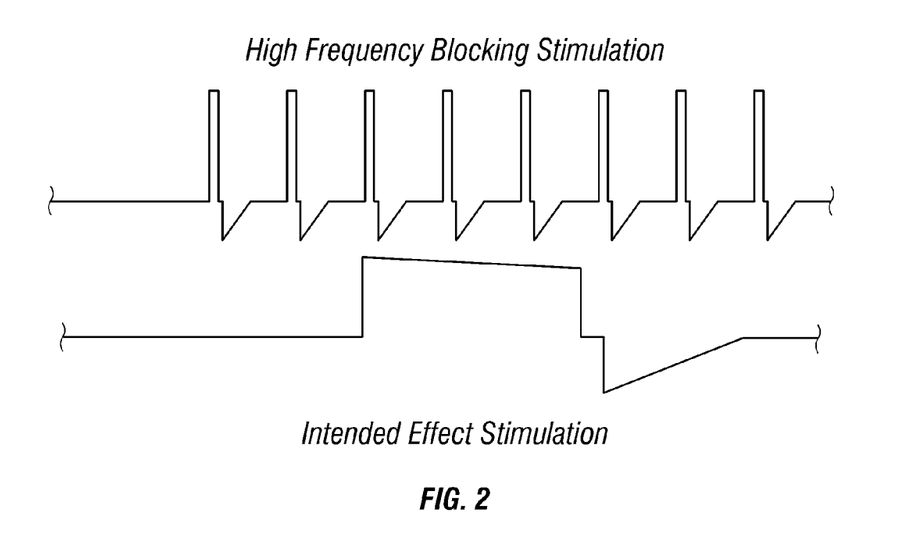
FIG. 2 shows blocking stimulation starting before and ending after intended effect stimulation.

FIG. 2 depicts high frequency blocking stimulation beginning earlier in time than the intended effect stimulation and continuing until after the intended effect stimulation has finished. By starting the high frequency blocking stimulation before and continuing it after the intended effect stimulation is applied, undesirable side effects associated with the intended effect stimulation may be blocked more effectively than would be possible if the high frequency blocking stimulation did not start until the same time as, or after, and/or stopped at the same time, or before, the intended effect stimulation. The intended effect stimulation may be a single pulse or multiple pulses.

Figure 3A:
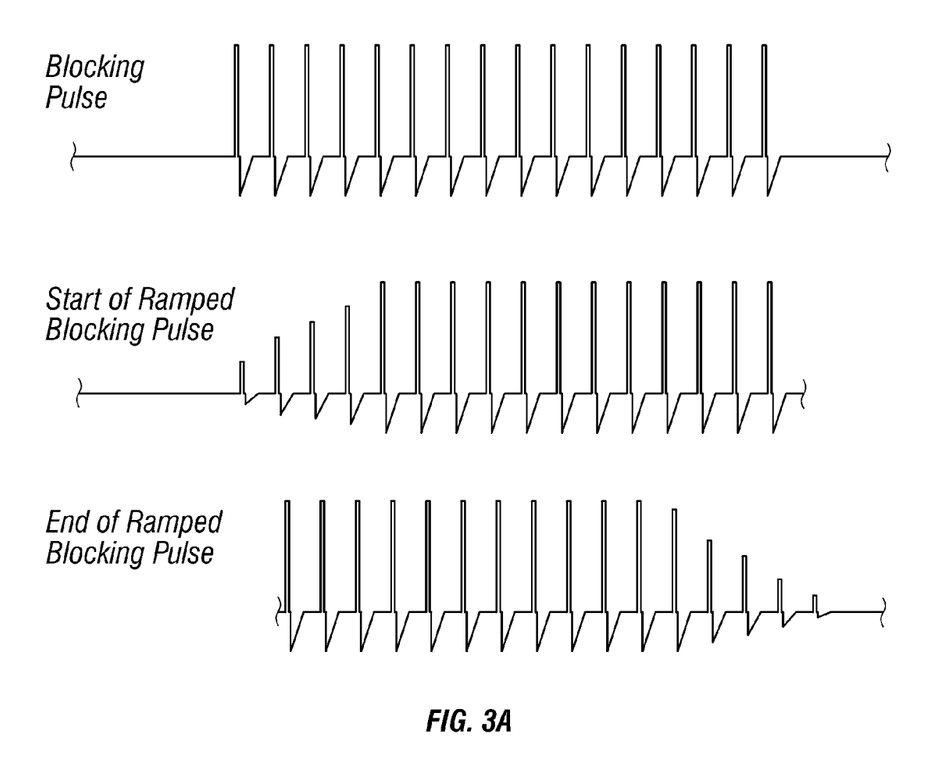
FIGS. 3a-3d show various combinations and permutations of high frequency and/or direct current blocking pulses with and/or without ramping at the beginning and/or end of the pulses.

The waveform at the top of FIG. 3a depicts high frequency blocking stimulation pulses that start and stop without any ramping or gradual increase or decrease of the amplitude of the pulses. The middle and lower waveforms, depict blocking pulse waveforms in which the amplitude of the waveform is ramped up or gradually increased at the beginning of the waveform, and ramped down or gradually decreased at the end of the waveform, respectively. Such ramping may be used in order to minimize creation of any action potentials that may be caused by more abruptly starting and/or more abruptly stopping the high frequency blocking stimulation.

Figure 3B:
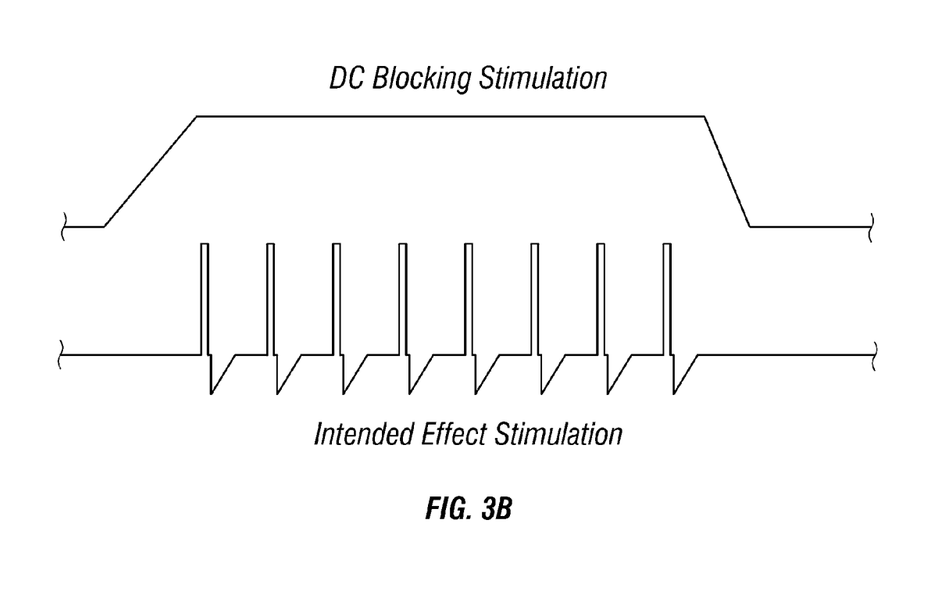

Creation of a blocking signal without action potentials being caused by the high frequency blocking pulses is desirable. As shown in FIG. 3b, a straight direct current pulse may be employed throughout the time for blocking. It may be depolarizing, especially if it has a gradual ramp that allows accommodation of the neural tissue to prevent action potentials from developing. Action potentials that approach the region run into areas where neuronal sodium gates are already affected and thus cannot open. It may also be of opposite sign, hyperpolarizing. This prevents action potentials from starting when the transmembrane potential cannot be sufficiently reduced to open the sodium channels, but action potentials approaching the region might still pass through.

A danger associated with direct current pulses is that there may be electrode dissolution and neuronal damage due to a steady and long distance flow of ions. However, such stimulation may be applied relatively infrequently, for instance just a few times per hour or per month, depending on the application. The ability to shield the side effects, therefore, may outweigh the dangers from intermittent direct current stimulation.

Figure 3C:
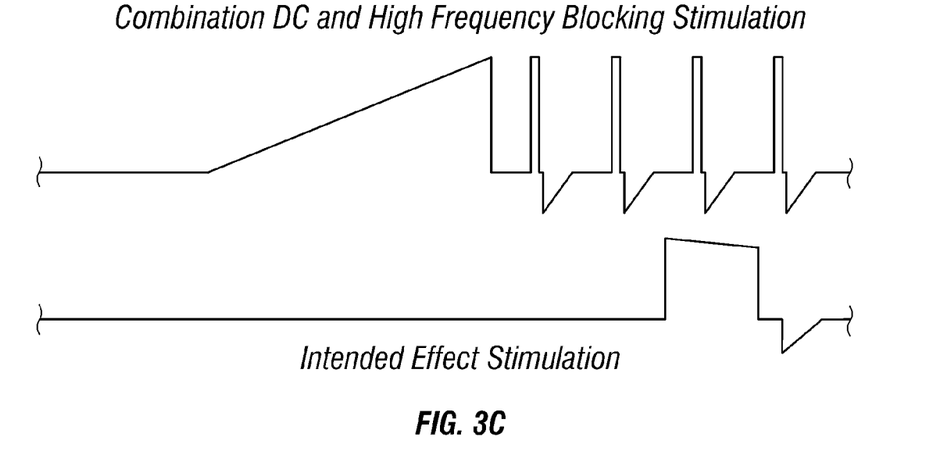

FIG. 3c shows a combination of modes for blocking. There is a gradual DC ramp and then a series of high frequency pulses. The ramp may produce accommodation of neurons, and prevent any action potentials. The continuation of high frequency stimulation may keep neurons deactivated, while still producing charge-balanced pulses. This technique may be used to advantage to prevent initial action potentials and to minimize electrode or tissue problems.

Figure 3D:
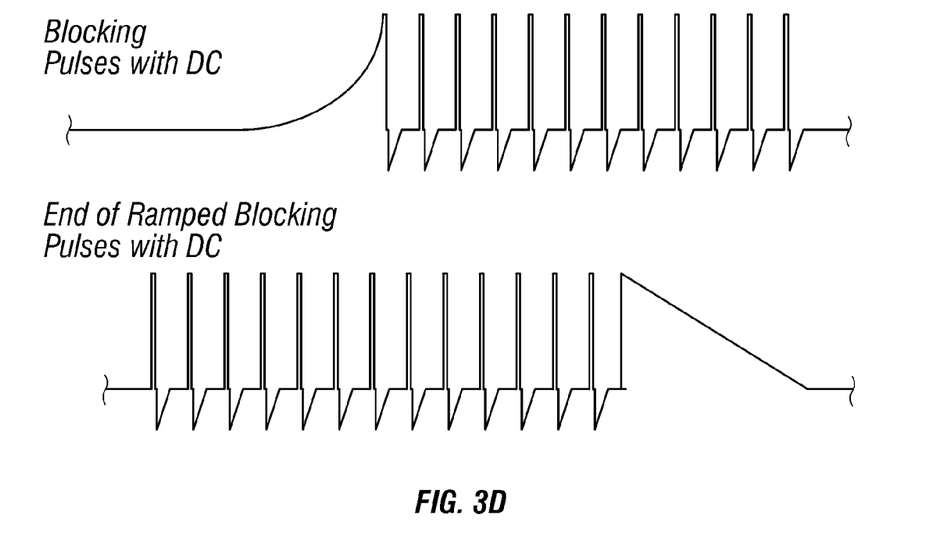

FIG. 3d shows multiple combinations with a variety of DC pulses. The initial pulse might have an exponential rise instead of a linear rise. The end of the blocking signal might also use a DC pulse to allow the neuronal tissue to return to its excitable state without causing activations, for example, anodal break.

Figure 4:
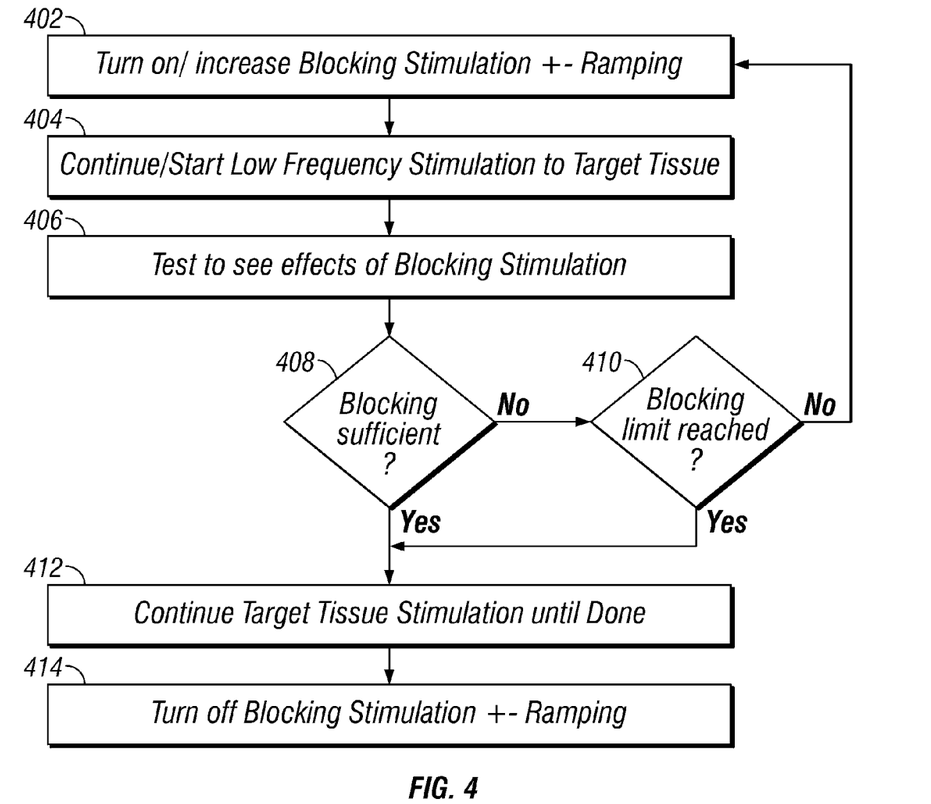
FIG. 4 is a flow chart depicting steps that may be performed to block activation of tissue in accordance with certain inventive principles.

FIG. 4 is a flow chart depicting steps that may be performed to block activation of tissue in accordance with certain inventive principles. At step 402, high frequency blocking stimulation is started and may optionally be ramped as described above with reference to FIG. 3. At step 404, low frequency intended effect stimulation is started. At step 406, a determination may be made as to how effectively the high frequency stimulation is blocking one or more undesirable side effects associated with the intended effect stimulation. This determination may be performed by a suitable sensor for measuring various parameters, such as movement of limb, contraction of sphincter, or any other suitable measurement indicating the degree to which an undesired side effect has been blocked.

If the blocking stimulation is determined to be insufficient, a determination is made as to whether a predetermined limit on the amount of blocking stimulation to be applied has been reached, as shown at 408 and 410. If the blocking stimulation limitation has not yet been reached, the blocking stimulation may be increased at step 402, the low frequency stimulation may be continued as shown in step 404, and the determinations may be made again as shown at 408 and 410.

If the blocking stimulation is determined to be sufficient, the intended effect, also referred to as target tissue, stimulation may be continued for as long as is desirable, as shown at 408 and 412. After terminating the intended effect stimulation at 412, the high frequency blocking stimulation may be terminated, as shown at 414.

Figure 5:
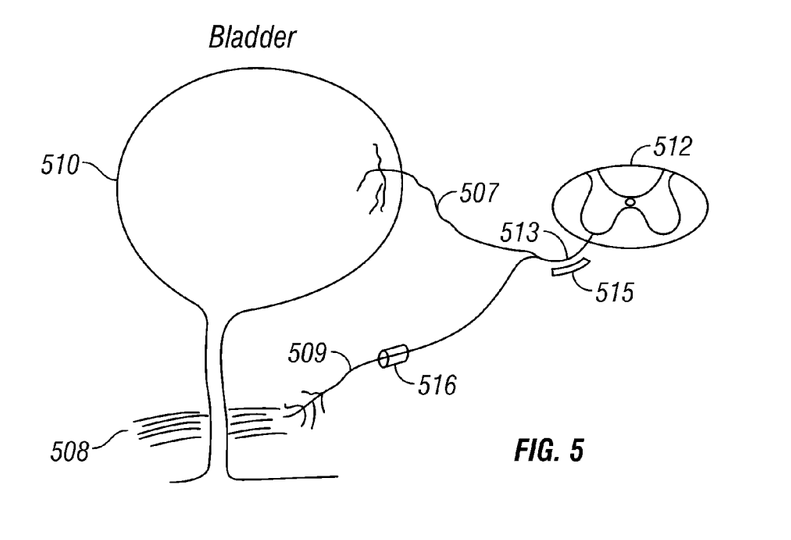
FIG. 5 is a schematic diagram showing electrode placement for promotion of micturition in accordance with various inventive principles.

Turning now to example applications of the principles of this invention, FIG. 5 is a schematic diagram showing electrode placement for promotion of micturition in accordance with various inventive principles. Anterior sacral root 513 is shown originating from spinal cord 512, which is shown in a sectional view. Electrode 515 is shown in close proximity to anterior sacral root (S1-S4) 513. Low frequency intended effect stimulation may be applied to sacral root 513 via electrode 515 in order to promote micturition by causing action potentials in nerve 507 leading to bladder 510. In order to block activation of external sphincter 508 of the urethra in the pelvic floor muscles of a patient, high frequency blocking stimulation may be applied near branch 509 of pudendal nerve leading to external sphincter 508. The high frequency blocking stimulation is preferably started before and continued after the application of the low frequency intended effect stimulation. In addition to the sacral roots, low frequency intended effect stimulation may also be applied to other parts of the patient's body, including, but not limited to, the patient's bladder dome and/or the patient's pelvic plexis of nerves. Sphincter contraction may also be prevented by application of high frequency blocking stimulation at locations other than the patient's pudendal nerve, including, but not limited to, the patient's sacral dorsal roots, spinal dorsal columns, conus medullaris, hypogastric plexus, and perineal nerve.

Figure 6:
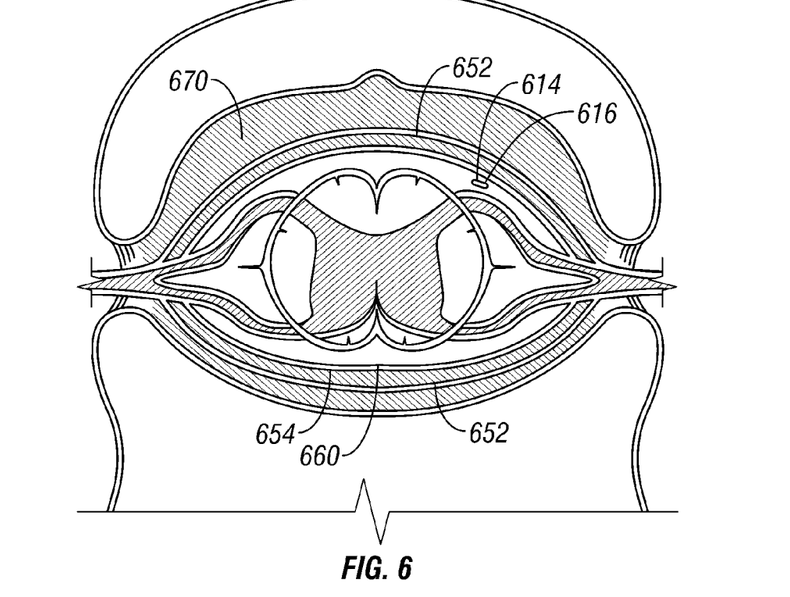
FIG. 6 is a schematic diagram showing electrode placement in a patient's intrathecal space near the patient's dorsal root for blocking sensations associated with stimulation of another part of the patient's body.

FIG. 6 is a schematic diagram showing placement of electrode 614 in a patient's intrathecal space near the patient's dorsal root for blocking sensations associated with stimulation of another part of the patient's body. As discussed in the Background of the Invention section above, stimulating nerves leading to bladder 510, without blocking activation of the external sphincter 508, may lead to reflex sympathetic dystrophy and stroke, among other complications. Rather than cut the afferent nerves, as has been proposed in U.S. patents to Tanagho and Schmidt et al. U.S. Pat. Nos. 4,607,639; 4,703,755; and 4,771,779)*, the dorsal roots may be stimulated at high frequency to block their activation while the bladder is contracting, thereby reversibly blocking activation of the dorsal root tissue, as shown in FIG. 6. In addition to preventing reflex sympathetic dystrophy, application of high frequency stimulation via lead 616 may prevent undesirable sensation associated with the low frequency stimulation applied to contract the patient's bladder by preventing activation of the patient's dorsal root. As will be apparent, undesirable sensations from many sources other than the patient's bladder may also be blocked in a similar manner. As will also be apparent, electrode 614 may also be placed in other suitable areas in order to block activation of other tissue thereby preventing other undesirable effects of low frequency intended effect stimulation applied elsewhere in a patient's body. For instance, electrode 614 may be placed outside the arachnoid membrane 660 in the subdural space 654 or outside dura 652 in the epidural space 670.

Blocking signals can be delivered at any of these sites to not only prevent pain, but also prevent nerve action potentials from entering the spinal cord and causing undesired reflexes. If pain is the chief undesired side effect from nerve or tissue activation, then it is possible to block it as it ascends the spinal cord near the surface of the ventrolateral quadrant, in the spinothalamic tract, on the opposite side of the spinal cord, since pain fibers cross near their point of origin. It may be advantageous to place an electrode under the dura, next to the pial surface in this case, to not also cause loss of sensations or motor control on that opposite side.

Figure 7:
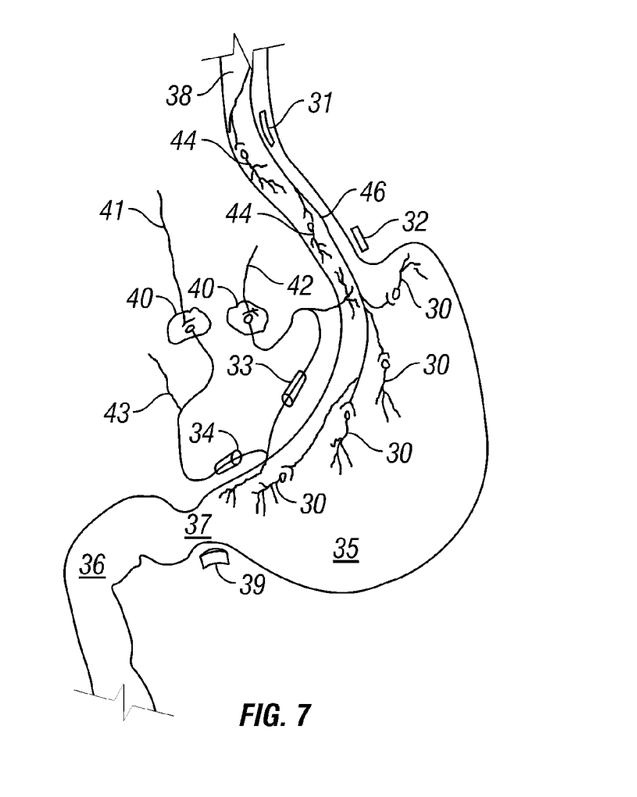
FIG. 7 is a schematic diagram showing electrode placement for assisting peristalsis of a patient's esophagus and/or emptying the patient's stomach.

FIG. 7 is a schematic diagram showing electrode placement for assisting peristalsis of a patient's esophagus and/or emptying the patient's stomach. Branches of vagus nerve 46 are shown along esophagus 38 and stomach 35 and connecting to myenteric nervous system 44, which are local neurons involved in peristaltic contraction of the esophagus. High frequency blocking stimulation may be applied via electrode 32 near the hiatal portion of the esophagus, which is where the bottom portion of the esophagus 38 meets upper portion of stomach 35. Low frequency intended effect stimulation may then be applied by upper electrode 31 to promote peristalsis of the esophagus in order to move food down the esophagus and into the stomach. The high frequency blocking stimulation will prevent the low frequency intended effect stimulation from undesirably causing the hiatal portion of the esophagus to contract. Peristalsis of the patient's esophagus may also be promoted by application of low frequency intended effect stimulation of the patient's pharynx. Contraction of the patient's gastroesphageal sphincter may be prevented by application of high frequency blocking stimulation to nerves leading to that portion of the patient's esophagus.

In a similar manner, contraction of pyloric sphincter 37 may be prevented by applying high frequency stimulation via electrode 39 while applying low frequency stimulation to the stomach muscle 35 or to electrodes 33 and 34 located in close proximity to descending branches of celiac ganglia 40 in order to move food from the patient's stomach 35 to the patient's intestine 36.

Peristalsis of the ureter, to move urine to the bladder, and the intestine, to move food materials along, are also normal physiological functions of the urinary and digestion system that may become compromised by trauma or disease. Although not depicted in FIG. 7, in these cases, there could be activation at low frequency to start the peristalsis of material. In the case of the ureter, the activation should be in the renal pelvis portion of the kidney, or near the top of the ureter, above any segment that is paralyzed, or at intact nerves going to those structures. In the case of the intestine, activation should be anywhere along the intestine that there is a functional problem, or at intact nerves going to that portion of bowel. Activation may have to be done in a delayed, sequential process along the length of the structure as well, to keep the peristalsis moving adequately. Blocking of excitation using high frequency stimulation and/or direct current potentials should be done where a particular valve may not be functionally opening as required. In the case of the ureter, this might be near the bladder's trigone, where an antireflux valve usually helps prevent urine flow back toward the kidney, or at intact nerves that innervate that portion of the bladder. In the case of the intestine, this might be at the ileocecal valve, or at nerves that go to that area of the intestine. In cases where peristalsis can be restored by low frequency activation and there is undesirable sensation being produced, blocking can be done on the dorsal columns or dorsal roots of sensory signals going to the spinal cord and brain. It is conceivable that blocking of tissue excitation should be done in two locations: at a nonfunctioning valve, to prevent excitation by the peristaltic wave, done at an appropriate time related to the speed of peristalsis and distances, and at the spinal sensory pathways, to prevent passage of action potentials, mostly useful near the time the desired peristalsis is begun by low frequency activation.

Figure 8:
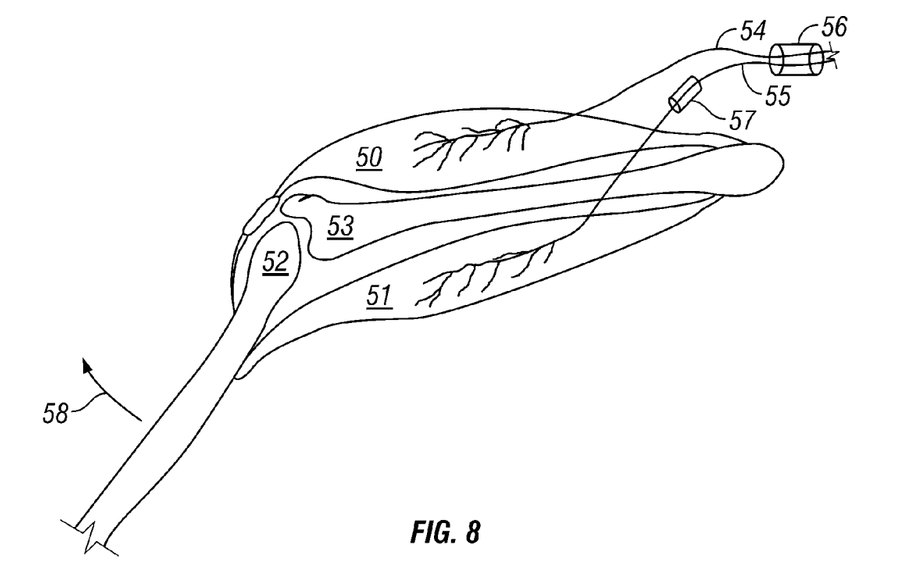
FIG. 8 is a schematic diagram showing electrode placement for extending a patient's lower leg.

Referring to FIG. 8, electrode placement is depicted for functional electrical stimulation to control muscles for extending a patient's leg. Nerve 54, leading to muscle 50, may be stimulated by electrode 56 causing muscle 50 to contract such that the patient's tibia 52 will move in the direction of arrow 58, thereby straightening the patient's leg. Such stimulation may undesirably cause simultaneous contraction of an antagonist muscle, such as muscle 51. Therefore, nerve 55 may be stimulated with high frequency blocking stimulation at electrode 57 to prevent action potentials in nerve 55 from causing contraction of muscle 51. As will be apparent applying varying levels of high frequency stimulation to muscle 51 may be desirable in order to move tibia 52 in a controlled fashion. The amount and/or duration of either or both types of stimulation may be controlled as described above in connection with FIG. 4. For example, when a person is standing up, tension in both muscles is desirable. Low frequency stimulation from electrode 56 may be applied to both nerves 54 and 55, while high frequency stimulation may be applied to modulate the action potentials that can get through to muscle 51, thereby reducing the amount of axons in nerve 55 that cause contraction of muscle 51.

Figure 9:
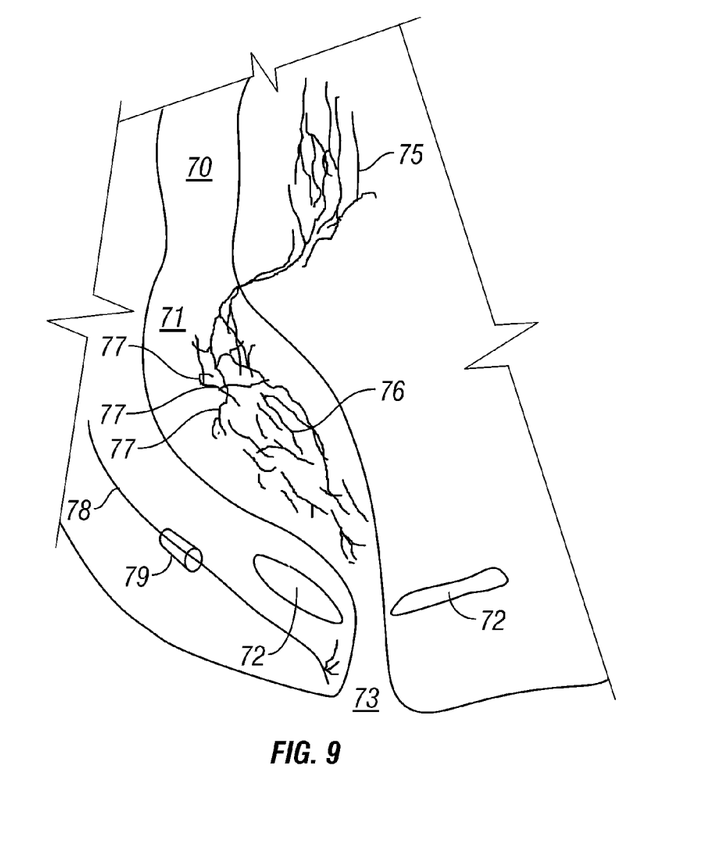
FIG. 9 is a schematic diagram showing electrode placement for promotion of defecation in accordance with various inventive principles.

FIG. 9 is a schematic diagram showing electrode placement for promotion of defecation in accordance with various inventive principles. Nerves 75 outside descending colon 70 and nerve plexus 76 in the wall of rectum 71 are shown. Low frequency stimulation in the area of pelvic plexus nerves to rectum 77, which could be used to contract the rectum to promote defecation, may also stimulate pudendal nerve 78, directly, or by reflex arc, in a similar manner as described above with respect to the bladder and FIG. 5. Accordingly, high frequency blocking stimulation may be applied via electrode 79 to pudendal nerve 78 to prevent action potentials in pudendal nerve 78, which would undesirably cause pelvic floor muscles or anal sphincter muscles 72 to contract. Pelvic plexus nerves 77 originate from the sacral roots as does the pudendal nerve 78. Using low frequency sacral root stimulation, pudendal nerve 78 will be activated at a lower amplitude than pelvic plexus nerves 77 because pudendal nerve 78 contains larger diameter axons. At higher amplitudes of low frequency stimulation the rectum may contract, but the pudendal nerve 78 will be activated and will prevent defecation. This phenomenon also applies to stimulation of the nerves discussed with respect to the bladder. Accordingly, the bladder and the rectum cannot be contracted with low frequency stimulation until its sphincter has already been undesirably contracted, absent high frequency blocking stimulation applied to a nerve leading to the sphincter. To promote defecation, low frequency intended effect stimulation may also be applied at other areas in a patient's body, including, but not limited to, the patient's hypogastric plexus, pelvic plexus, nerves along the patient's rectum, and sacral roots. Undesired side effects of such low frequency intended effect stimulation, may include, but are not limited to, sphincter contraction, elevation of the pelvic floor, and promotion of a sharp ano-rectal angle. These can be prevented by application of high frequency or direct current blocking stimulation to other part or the patient's body, including, but not limited to, the patient's sacral dorsal roots, spinal dorsal columns, conus medullaris, and nerves to the patient's pelvic floor muscles.

As mentioned above, defibrillation of a patient's heart by use of strong electric pulses is extremely painful. Commonly assigned U.S. Pat. No. 5,817,131, which issued to Elsberry et al. and is incorporated herein by reference, discloses blocking of pain messages using spinal cord stimulation or stimulation in other sites in peripheral or central pathways. The Elsberry '131 patent discloses blocking of pain messages via the Gate Control Hypothesis, which involves stimulation typically at a frequency below 100 Hz near the doral columns. Presumably, larger diameter fibers are stimulated to block the smaller diameter fibers, which carry pain and temperature. In accordance with the principles of the instant invention, high frequency stimulation, in other words, stimulation at frequencies above 100 Hz, may be used to block substantially all afferent nerves near the heart, including the small diameter fibers which often carry pain messages. High frequency or direct current blocking stimulation may preferably be applied to peripheral nerves, including nerves from the heart, such as vagus or sympathetic nerves or both, which tend to have small diameter axons.

Figure 10:
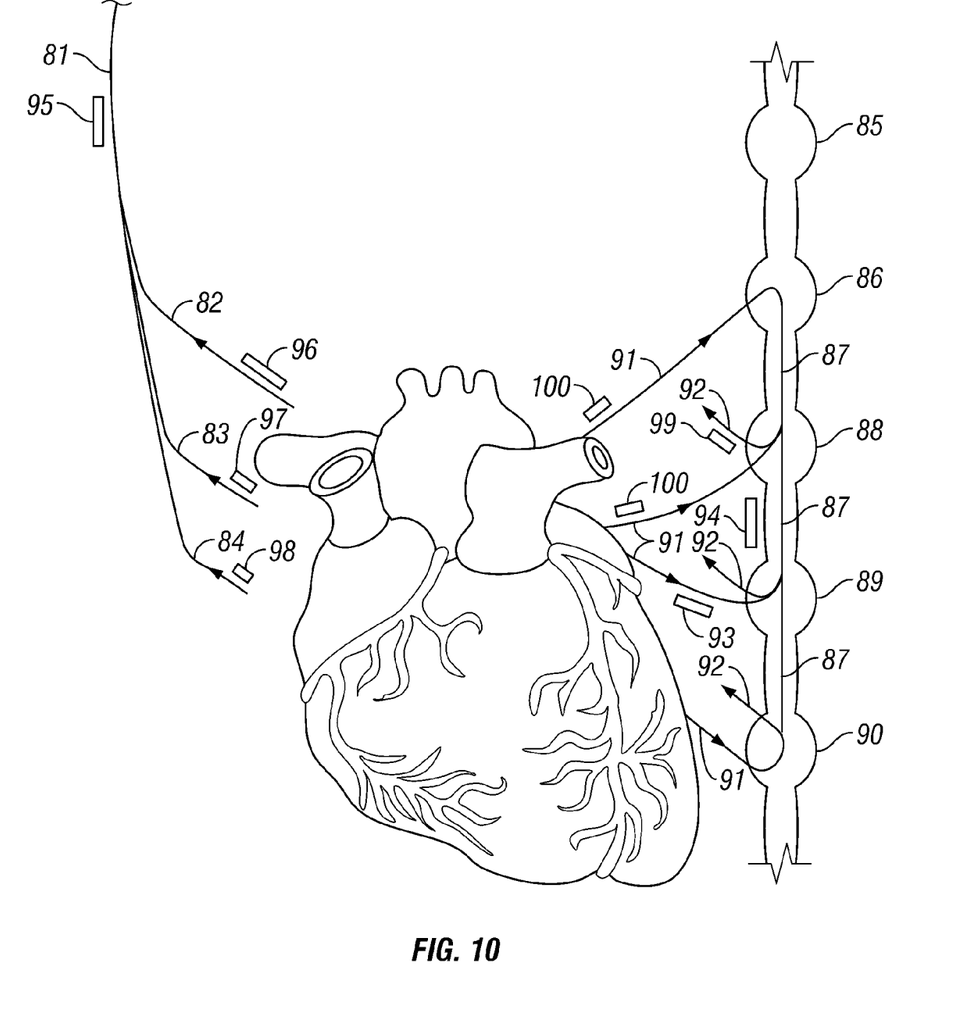
FIG. 10 is a schematic diagram showing suitable electrode placement for reducing pain perceived by a patient associated with defibrillation pulses.

FIG. 10 is a schematic diagram showing suitable electrode placement for reducing pain perceived by a patient associated with defibrillation pulses. Pain information may travel from the heart by going to the left in FIG. 10 through the parasympathetic vagus nerve 81 due to its branches, 82-84. Pain information may also travel from the heart to the right in FIG. 10 into the sympathetic system via nerves exiting the heart 91. These nerves bring information, especially about pain, to the stellate sympathetic ganglia 85 or to the T1-T4 thoracic ganglia 86, 88, 89, and 90. In order to block pain signals in sympathetic efferent nerves 91, electrodes could be placed near those nerves either before, 93 and 100, or after, 94 and 99, they pass to the sympathetic ganglia 85, 86, 88, 89, and 90. These electrodes may be placed endoscopically using a needle near the branches of these nerves. While defibrillating a patient's atria or ventricles, low frequency intended effect stimulation may be applied via a heart pacing/defibrillation lead inside the patient's heart chambers or via a heart pacing/defibrillation lead outside the patient's heart chambers. Pain associated with defibrillating a patient's atria or ventricles may be prevented by application of high frequency or direct current blocking stimulation to locations within the patient's body including, but not limited to, the bilateral vagus nerves, branches of the patient's vagus nerves near the patient's heart, sympathetic nerves near the heart, ansa subclavia, sympathetic trunk ganglia (T1-T4), stellate ganglia, cervical ganglia, celiac plexus, brachial plexi, dorsal columns and dorsal roots (C1-T4).

If the ventricles are being defibrillated, blocking stimulation may be applied to lower ganglia 89 and 90 via electrode 93, for example. Atrial defibrillation, on the other hand, will typically be needed more often, for instance many times per day. High frequency stimulation may be applied to electrodes 94, 99 or 100 for the upper sympathetic ganglia 85, 86, 88 and electrode 96, 97 or 98 may be used for blocking pain information transmitted via the vagus nerve, depending upon where defibrillation occurs.

The preferred embodiments may be altered or amended without departing from the true spirit and scope of the invention, as defined in the accompanying claims.

I claim:

1. A method of blocking undesirable side effect activation of electrically excitable tissue, the method comprising the steps of:

therapeutically activating tissue at a first predetermined site within a patient's body; and blocking activation of tissue or conduction of action potentials at a second predetermined site within the patient's body by applying high frequency stimulation or one or more direct current pulses or both high frequency stimulation and one or more direct current pulses at or near the second site, wherein the undesired effect is muscle contraction:

the desired effect is peristalsis of the patient's ureter; and the undesired side effect is closure of the patient's anti-reflux valves near the patient's bladder trigone.

2. The method of claim 1, wherein: the first site is selected from the group consisting of the patient's: renal pelvis and a portion of the patient's ureter.

3. The method of claim 1, wherein: the second site is the base of the patient's bladder near an entrance of the ureter, hypogastric plexus, and pelvic plexus.

4. A method of blocking undesirable side effect activation of electrically excitable tissue, wherein such undesirable side effect activation includes muscle contraction, the method comprising the steps of:

therapeutically activating tissue at a first predetermined site within a patient's body by applying low frequency stimulation at or near the first predetermined site; and blocking activation of tissue or conduction of action potentials at a second predetermined site within the patient's body by applying high frequency stimulation or one or more direct current pulses or both high frequency stimulation and one or more direct current pulses at or near the second site such that the high frequency stimulation and/or the direct current pulses prevent the low frequency stimulation applied at the first site from activating the electrically excitable tissue, or causing conduction of action potentials, at the second site, wherein:

the desired effect is peristalsis of the patient's ureter and the first site is selected from the group consisting of the patient's: renal pelvis and a portion of the patient's ureter; and the undesired side effect is closure of the patient's anti-reflux valves near the patient's bladder trigone and the second site is the base of the patient's bladder near an entrance of the ureter, hypogastric plexus, and pelvic plexus.

5. The method of claim 4, wherein the high frequency stimulation or the direct current pulses or both the high frequency stimulation and the direct current pulses begin before and continue during the therapeutic activation.

6. The method of claim 4, wherein the high frequency stimulation or the direct current pulses or both the high frequency stimulation and the direct current pulses begin with a relatively low amplitude and the amplitude is gradually increased.

7. The method of claim 4, wherein the high frequency stimulation or the direct current pulses or both the high frequency stimulation and the direct current pulses are terminated by gradually reducing the amplitude of the high frequency stimulation or the direct current pulses or both the high frequency stimulation and the direct current pulses.

8. The method of claim 4, further comprising the steps of:

sensing a state of the tissue at the second site or at a site that is remote from both the first site and the second site; and in response to the sensing step, adjusting at least one parameter of the high frequency stimulation or the direct current pulses or both the high frequency stimulation and the direct current pulses, the parameter being selected from the group consisting of: pulse amplitude, pulse width, pulse frequency, pulse duty cycle, pulse polarity, and pulse waveform.

9. The method of claim 8, further comprising:

sensing a state of the tissue at the second site or at a site remote from both the first site and the second site; and in response to an indication from the sensor that tissue at the second site is activated, applying the high frequency stimulation or the direct current pulses or both the high frequency stimulation and the direct current pulses to the second site.

* * * * *